United States Patent
Pasha

(10) Patent No.: US 11,803,754 B2
(45) Date of Patent: Oct. 31, 2023

(54) SPINAL SURGERY OUTCOME PREDICTION

(71) Applicant: Medtronic Sofamor Danek USA, Inc., Memphis, TN (US)

(72) Inventor: Saba Pasha, Houston, TX (US)

(73) Assignee: MEDTRONIC SOFAMOR DANEK USA, INC., Memphis, TN (US)

(*) Notice: Subject to any disclaimer, the term of this patent is extended or adjusted under 35 U.S.C. 154(b) by 377 days.

(21) Appl. No.: 17/260,410

(22) PCT Filed: Jul. 15, 2019

(86) PCT No.: PCT/US2019/041794
§ 371 (c)(1),
(2) Date: Jan. 14, 2021

(87) PCT Pub. No.: WO2020/018417
PCT Pub. Date: Jan. 23, 2020

(65) Prior Publication Data
US 2021/0264601 A1  Aug. 26, 2021

Related U.S. Application Data

(60) Provisional application No. 62/698,387, filed on Jul. 16, 2018.

(51) Int. Cl.
*A61B 34/10* (2016.01)
*G06T 7/70* (2017.01)
(Continued)

(52) U.S. Cl.
CPC .............. *G06N 3/08* (2013.01); *A61B 34/10* (2016.02); *G06F 18/22* (2023.01);
(Continued)

(58) Field of Classification Search
CPC .......... G06N 3/043; G06N 3/08; G06N 20/00; A61B 34/10; A61B 34/20; A61B 34/30;
(Continued)

(56) References Cited

U.S. PATENT DOCUMENTS 11,000,334 B1* 5/2021 Young .................. G06T 7/251
2007/0242869 A1* 10/2007 Luo .................... G06T 7/0012
382/132

(Continued)

OTHER PUBLICATIONS

Kadoury et al., "3D Morphology Prediction of Progressive Spinal Deformities from Probabilistic Modeling of Discriminant Manifolds," IEEE, Jan. 17, 2017, 11 pages.
(Continued)

*Primary Examiner* — Nay A Maung
*Assistant Examiner* — Jose M Torres
(74) *Attorney, Agent, or Firm* — FOX ROTHSCHILD LLP

(57) ABSTRACT

A spinal surgery training process includes the steps of capturing a plurality of 2D images for each of a plurality of spines, generating a curve of each spine from the respective 2D images based on locations of select vertebrae in each of the spines, grouping the spines into one of a number of groups based on similarity to produce groups of spines having similarities, performing the capturing, generating, determining and grouping steps at least once prior to surgery and at least once after surgery to produce pre-operative groups and their resultant post-operative groups, and assigning surgical methods and a probability to each of the post-operative groups indicating the probability that a spinal shape of the post-operative group can be achieved using the surgical methods. An outcome prediction process for determining surgical methods can be implemented once the training process is complete.

20 Claims, 17 Drawing Sheets

(51) Int. Cl.

| | |
|---|---|
| *G16H 20/40* | (2018.01) |
| *G16H 50/20* | (2018.01) |
| *G16H 30/40* | (2018.01) |
| *G06T 7/00* | (2017.01) |
| *G06T 17/00* | (2006.01) |
| *G06F 18/22* | (2023.01) |
| *G06F 18/23213* | (2023.01) |
| *G06V 10/762* | (2022.01) |
| *G06V 10/82* | (2022.01) |
| *G06V 10/44* | (2022.01) |
| *G06V 20/64* | (2022.01) |
| *A61B 34/30* | (2016.01) |
| *A61B 90/00* | (2016.01) |
| *G06N 3/08* | (2023.01) |
| *G06N 20/00* | (2019.01) |

(52) U.S. Cl.
CPC ....... *G06F 18/23213* (2023.01); *G06N 20/00* (2019.01); *G06T 7/0014* (2013.01); *G06T 7/70* (2017.01); *G06T 17/00* (2013.01); *G06V 10/454* (2022.01); *G06V 10/763* (2022.01); *G06V 10/82* (2022.01); *G06V 20/647* (2022.01); *G16H 20/40* (2018.01); *G16H 30/40* (2018.01); *G16H 50/20* (2018.01); *A61B 34/30* (2016.02); *A61B 2034/105* (2016.02); *A61B 2090/367* (2016.02); *G06T 2207/20076* (2013.01); *G06T 2207/20081* (2013.01); *G06T 2207/30012* (2013.01); *G06V 2201/033* (2022.01)

(58) Field of Classification Search
CPC ........ A61B 2034/104; A61B 2090/367; G06F 18/22; G06F 18/23213; G06T 7/0014; G06T 7/70; G06T 17/00; G06T 2207/20076; G06T 2207/20081; G06T 2207/30012; G06V 10/454; G06V 10/763; G06V 10/82; G06V 20/647; G06V 2201/033; G16H 20/40; G16H 30/40; G16H 40/63; G16H 50/20; G16H 50/70

See application file for complete search history.

(56) References Cited

U.S. PATENT DOCUMENTS

| | | | |
|---|---|---|---|
| 2009/0226055 A1* | 9/2009 | Dankowicz | G06T 7/0012 382/128 |
| 2012/0143090 A1* | 6/2012 | Hay | A61B 6/505 600/587 |
| 2014/0323845 A1* | 10/2014 | Forsberg | G06T 7/60 600/407 |
| 2015/0287184 A1 | 10/2015 | Parent et al. | |
| 2016/0338685 A1 | 11/2016 | Nawana et al. | |
| 2018/0310993 A1* | 11/2018 | Hobeika | A61B 34/10 |
| 2020/0038109 A1* | 2/2020 | Steinberg | G16H 50/50 |
| 2020/0261156 A1* | 8/2020 | Schmidt | G06T 19/20 |
| 2020/0352651 A1* | 11/2020 | Junio | A61B 34/10 |
| 2021/0282862 A1* | 9/2021 | Bourlion | A61B 34/10 |

OTHER PUBLICATIONS

Mandel et al., "Spatiotemporal Manifold Prediction Model for Anterior Vertebral Body Growth Modulation Surgery in Idiopathic Scoliosis," Jun. 6, 2018, 9 pages, https://arxiv.org/abs/1806.02285.
Pasha et al., "Data-driven Classification of the 3D Spinal Curve in Adolescent idiopathic Scoliosis with an Applications in Surgical Outcome Prediction," Scientific Reports (2018)8:16296, Nov. 2, 2018, www.nature.com/scientificreports/, 10 pages.
Stokes et al., "Classification of Scoliosis Deformity 3-D Spinal Shape by Cluster Analysis," NIH Public Access Author Manuscript, Spine, Mar. 15, 2009; 34(6): 584-590, 17 pages.
International Search Report and Willien Opinion issued in PCT/US19/41794, dated Oct. 8, 2019, 8 pages.
Sun, Jing Chuan et al: "Can K-Line Predict the Clinical Outcome of Anterior Controllable Antedisplacement and Fusion Surgery for Cervical Myelopathy Caused by Multisegmental Ossification of the Posterior Longitudinal Ligament?", World Neurosurgery, Elsevier, Amsterdam, NL, vol. 116, Apr. 27, 2018 (Apr. 27, 2018), XP085435171, ISSN: 1878-8750, DOI: 10.1016/J.WNEU.2018.04.128.
Schwab, Frank J. et al: "Predicting Outcome and Complications in the Surgical Treatment of Adult Scoliosis :", Spine : an international journal for the study of the spine, vol. 33, No. 20, Sep. 1, 2008 (Sep. 1, 2008), pp. 2243-2247, XP055922035 US; ISSN: 0362-2436, DOI: 10.1097/BRS. 0b013e31817d1d4e.
EP Search Report in Application No. 19837122.1 dated May 30, 2022.
International Preliminary Report on Patentability and Written Opinion issued in International Application No. PCT/US2019/041794, dated Jan. 19, 2021, 8 pages.

\* cited by examiner

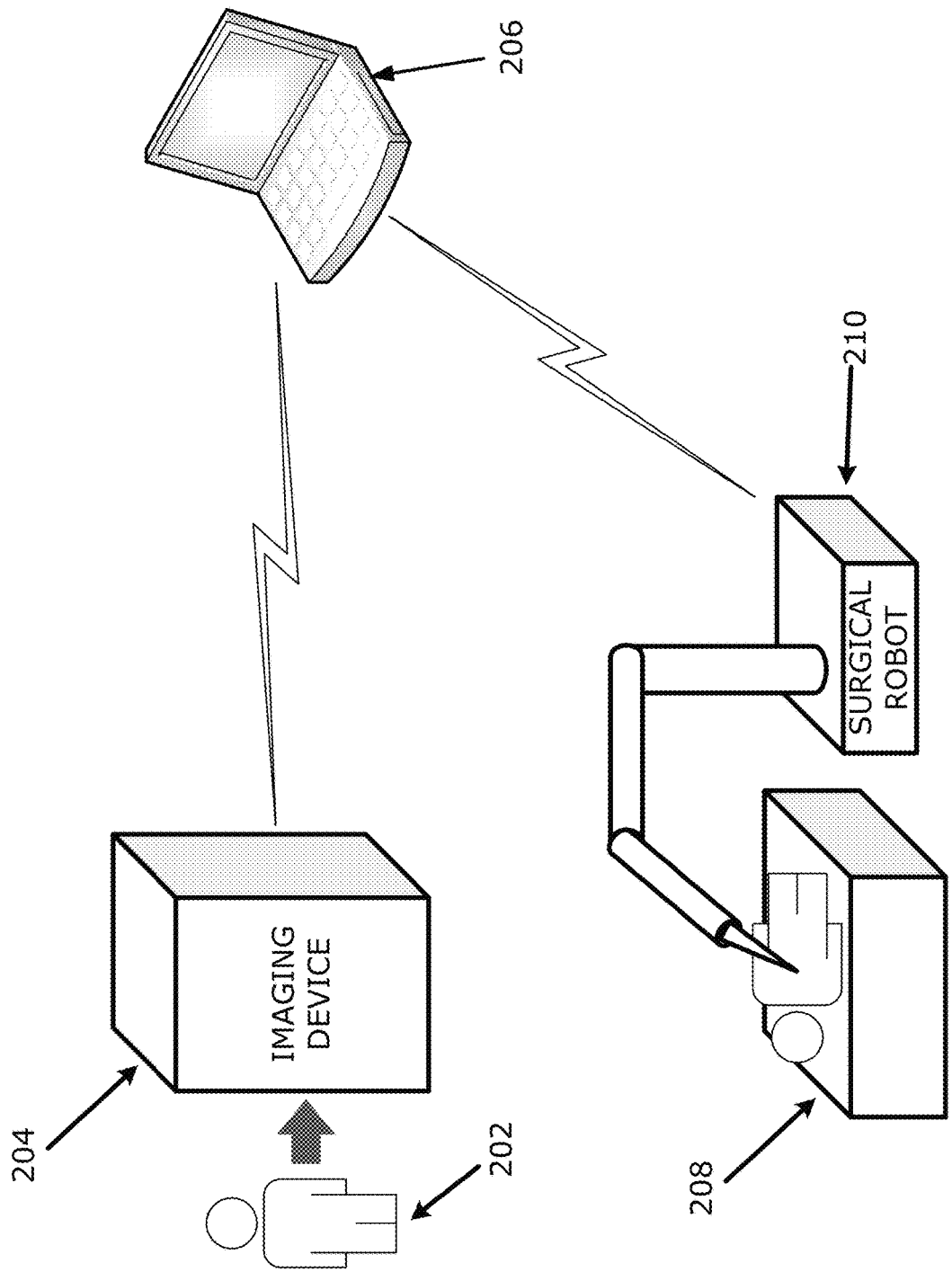

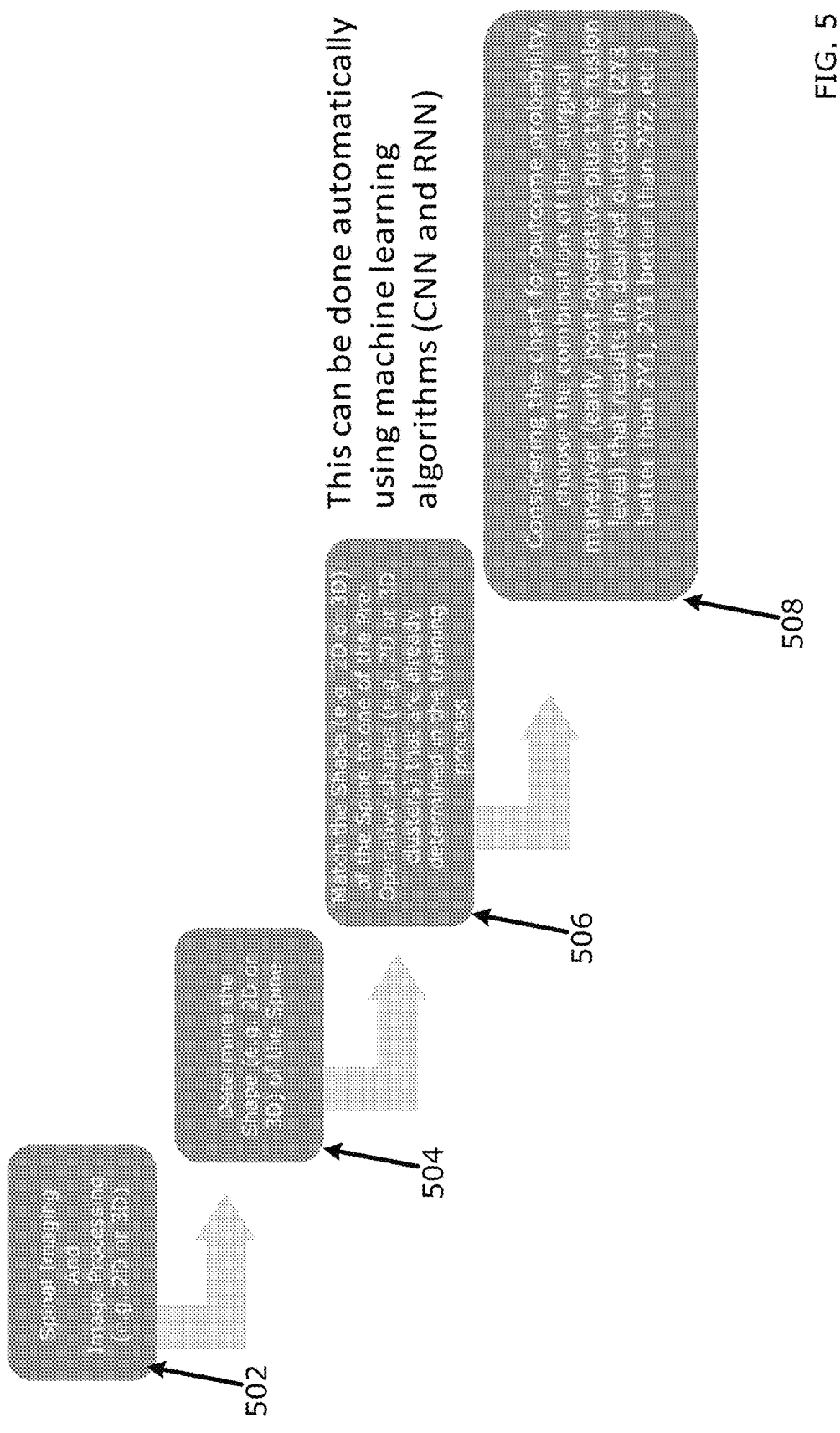

SPINAL SURGERY OUTCOME PREDICTION

CROSS-REFERENCE TO RELATED APPLICATIONS

This application is a U.S. National Phase Application of PCT/US2019/041794, filed Jul. 15, 2019, which claims the benefit of U.S. Provisional Application No. 62/698,387, filed Jul. 16, 2018, the contents of which are incorporated herein by reference in their entirety for all purposes.

FIELD

The subject matter disclosed herein relates to devices, systems and methods for performing outcome prediction for spinal surgery techniques.

BACKGROUND

Spinal surgery for correcting spinal curvature (e.g., curvature due to Scoliosis) includes various surgical techniques and parameters that result in different outcomes for a given patient. Choosing the best techniques and parameters for a given patient is therefore important. Typically, medical doctors observe physical characteristics (e.g., curvature) via X-rays of the patient's spine and attempt choose the surgical techniques and parameters that they believe will produce the best long term results for a given patient. However, the accuracy for this type of subjective prediction is highly dependent on various factors including the experience of the doctor, which often leads to prediction inaccuracies.

SUMMARY

An embodiment includes a spinal surgery training method comprising the steps of capturing, by an imaging device, a plurality of 2D images for each of a plurality of spines, generating, by a processor, a curve of each spine from the respective 2D images based on locations of select vertebrae in each of the spines, grouping, by the processor, the spines into one of a number of groups based on similarity to produce groups of spines having similarities, performing, by the imaging device and the processor, the capturing, generating, determining and grouping steps at least once prior to surgery and at least once after surgery to produce pre-operative groups and their resultant post-operative groups, and assigning, by the processor, surgical methods and a probability to each of the post-operative groups indicating the probability that a spinal shape of the post-operative group can be achieved using the surgical methods.

An embodiment includes a spinal surgery outcome prediction method comprising the steps of capturing, by an imaging device, a plurality of 2D images for a spine, generating, by a processor, a curve of the spine from the 2D images based on locations of select vertebrae in the spine, comparing, by the processor, the locations of the select vertebrae to pre-operative groups of other spines, wherein the pre-operative groups are associated by a probability with post-operative groups of the other spines, the probability indicating that a spinal shape of the post-operative group can be achieved using select surgical methods on a spine that is similar to the spines in the pre-operative groups, matching, by the processor, the spine to a subset of the pre-operative groups based on similarities between the spine and the other spines in the pre-operative group, and choosing, by the processor, the select surgical methods associated with one of the matching post-operative groups selected based on the probability.

An embodiment includes a spinal surgery training system comprising an imaging device configured to capture a plurality of 2D images for each of a plurality of spines. The system also includes a processor configured to generate a curve of each spine from the respective 2D images based on locations of select vertebrae in each of the spines, and group the spines into one of a number of groups based on similarity to produce groups of spines having similarities. The imaging device and the processor are further configured to perform the capturing, generating, determining and grouping steps at least once prior to surgery and at least once after surgery to produce pre-operative groups and their resultant post-operative groups. The processor is further configured to assign surgical methods and a probability to each of the post-operative groups indicating the probability that a spinal shape of the post-operative group can be achieved using the surgical methods.

An embodiment includes a spinal surgery outcome prediction system comprising a processor configured to generate a curve of the spine from a plurality of 2D images based on locations of select vertebrae in the spine, and compare the locations of the select vertebrae to pre-operative groups of other spines. The pre-operative groups are associated by a probability with post-operative groups of the other spines. The probability indicating that a spinal shape of the post-operative group can be achieved using select surgical methods on a spine that is similar to the spines in the pre-operative groups. The processor is further configured to match the spine to a subset of the pre-operative groups based on similarities between the spine and the other spines in the pre-operative group, and choose the select surgical methods associated with one of the matching post-operative groups selected based on the probability. Also included is a surgical robot configured to be controlled based on the chosen surgical methods.

BRIEF DESCRIPTION OF THE FIGURES

FIG. 2A is a view of a system for training an outcome prediction algorithm, predicting results of surgical methods, and performing spinal surgery based on the outcome prediction, according to an aspect of the disclosure.

FIG. 5 is a flowchart describing the outcome prediction process, according to an aspect of the disclosure.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and circuitry have been described at a relatively high-level, without detail, in order to avoid unnecessarily obscuring aspects of the present teachings.

INTRODUCTION

Adolescent idiopathic scoliosis (AIS) is a three-dimensional (3D) deformity of the spinal column with an onset around puberty. Although the pathomechanisms associated with development and progression of AIS remain unclear, non-surgical and surgical treatment options have been used to prevent the spinal deformity progression. The most common surgical technique realigns a part or the entire spine and secures it with a metal rod posteriorly, which results in ossification (fusion) of the vertebral bodies and stabilization of the curve. The success of the surgical treatment of AIS is evaluated with patient's postural balance, function and mobility, and absence of primary or compensatory curve progression, patients' satisfaction, and quality of life at long-term follow-ups.

Figure 1A:
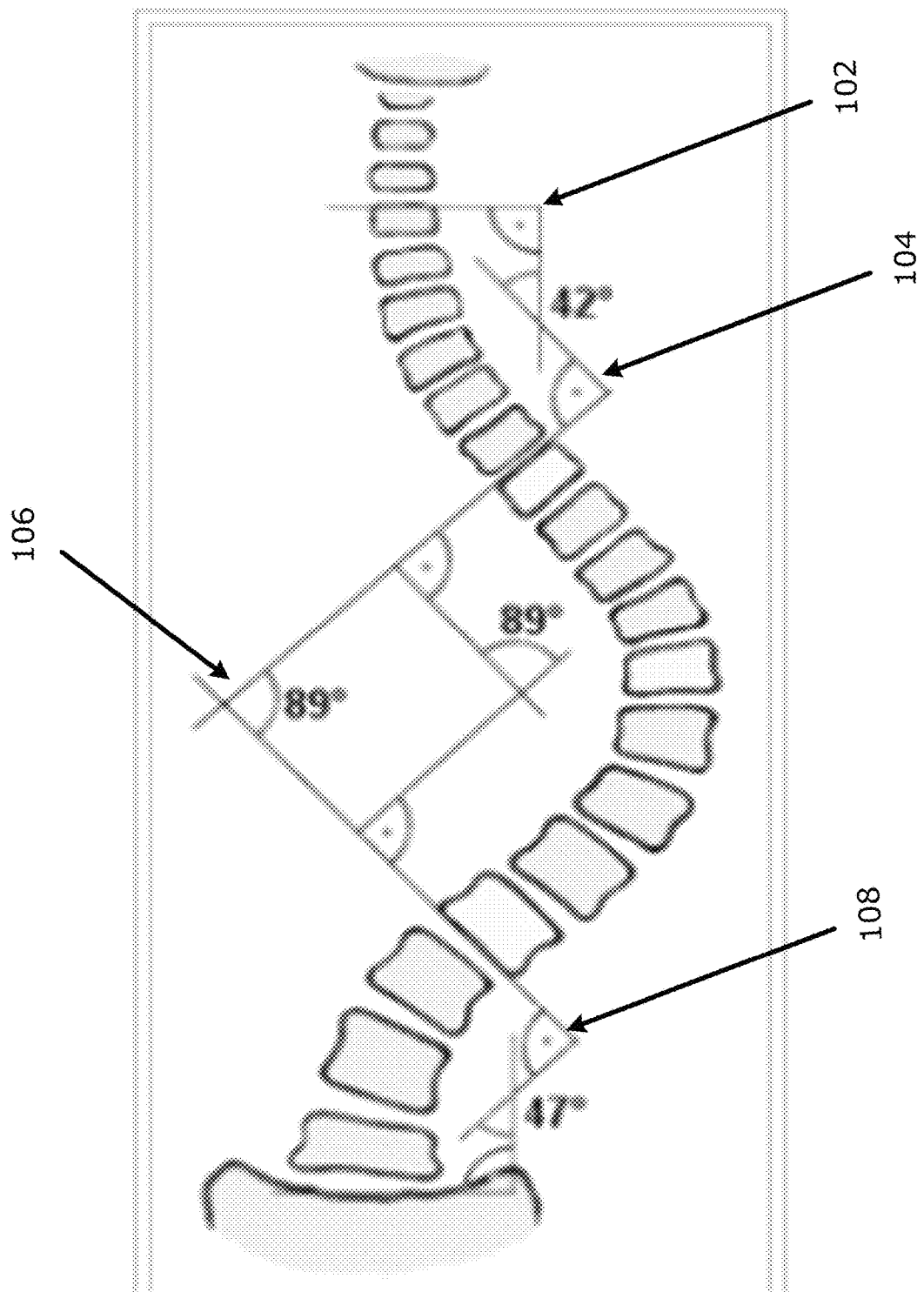
FIG. 1A is a view of a spine suffering from scoliosis, according to an aspect of the disclosure.

FIG. 1A is an example view of a spine suffering from AIS. The spine includes angles 102, 104, 106 and 108, also known as "Cobb Angles." As described above, AIS is a condition of spinal deformity consisting of lateral curvature and rotation of spine usually defined as a Cobb angle of 10 degrees or more.

Figure 1B:
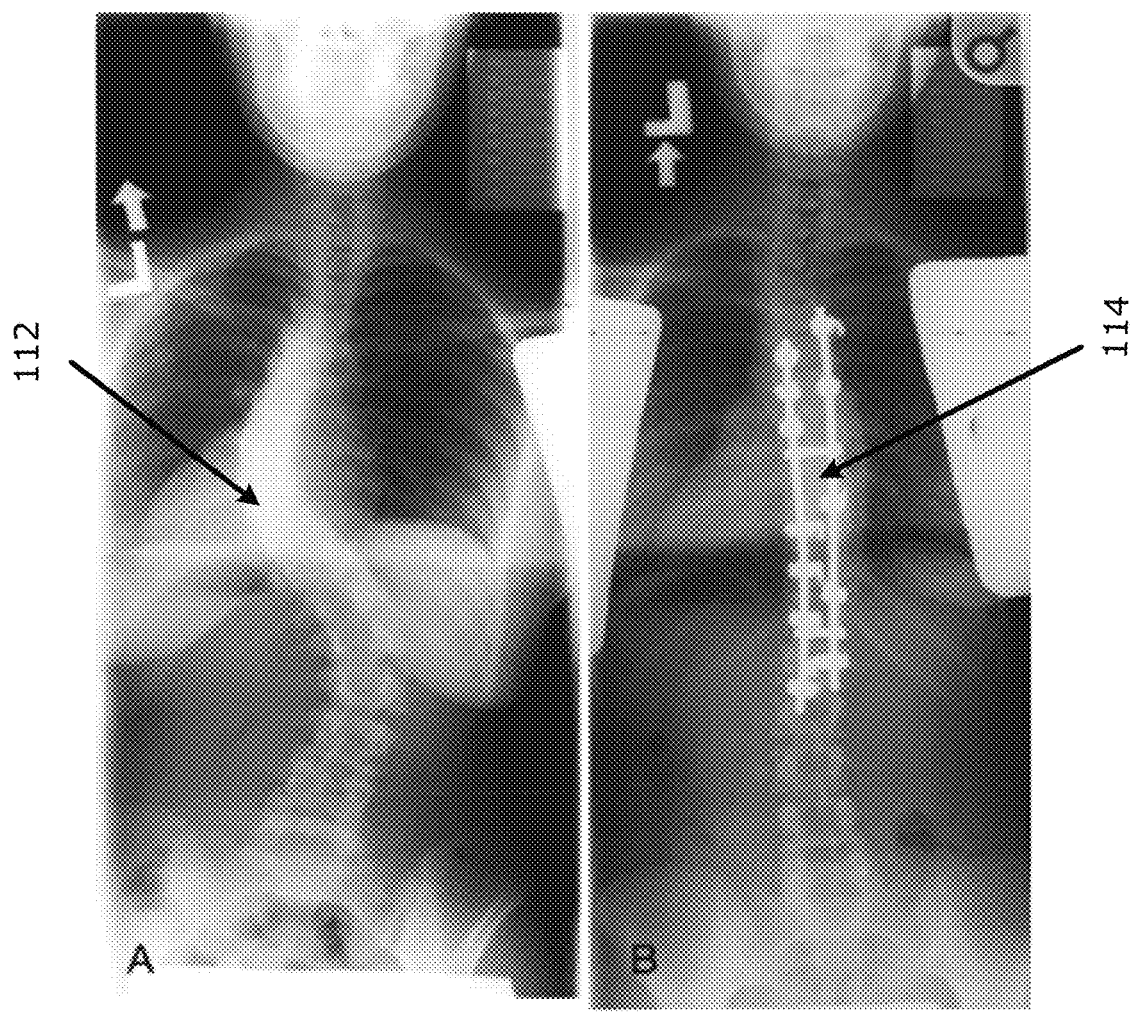
FIG. 1B is a comparison view of a scoliosis spine pre-op and post-op, according to an aspect of the disclosure.

As described above, metal rods are inserted during surgery to straighten the spine. FIG. 1B is a comparison view of a spine pre-operation (pre-op) and post-operation (post-op). As shown, pre-op spine 112 is curved with large Cobb angles. In contrast, the post-op spine 114 is straight due to the support of metal rods and screws holding the spine in a particular orientation.

Surgical planning is performed by the spinal surgeons prior to surgery. The physical characteristics (e.g., curvature, flexibility, angles, etc.) of the spine are analyzed to determine surgical methods. These surgical methods include but are not limited to vertebrae selection, rod/screw placement on particular vertebrae, and fusion of select vertebrae.

In order to guide the surgical planning which includes selecting the fusion levels, derotation of the spine, and imparting the sagittal curvature of the spine (kyphosis, lordosis), several guidelines based on the shape of the spine before surgery have been developed. Because the two-dimensional (2D) spinal images (e.g., X-rays) remain the mainstay in clinical diagnosis of the AIS patients, conventional surgical decision making guidelines are mainly based on the 2D shape of the spine, resulting in potentially erroneous assessment of the curve. Furthermore, identifying the curve types remain largely subjective, influenced by the observer interpretation, and inter-observer variability. An objective method that can describe the 3D outcome of the scoliosis surgery at long-term follow-ups as well as their association to the pre-op shape of the spine and the surgical intervention would be beneficial. The successful prediction of the outcome can improve the patient satisfaction and reduces the costs and risks associated with a need for revision surgery.

As the 3D curvature of the spine can explain a large amount of variability in the spinal alignment between the patients, a 3D classification of the overall spinal curvature, as opposed to the segmental uni-planar measurements of the curve projection, can classify the true curvature of the spinal deformity in AIS patients. Similarly, considering the true 3D spinal curve can explain the differences in the surgical outcomes by eliminating the need for evaluating the surgical outcomes based on only a limited number of 2D radiographic parameters. Patient classification based on the 3D spinal curvature can reduce the errors associated with the subjective 2D classification by objectively using the 3D overall shape of the spine.

The system and methods described herein teach an objective, data-driven framework for classification-based outcome prediction of the spinal surgery in AIS. More specifically, the framework is focused on determining treatment pathways, comprised of the variables that can be identified prior to the surgery or modified during the surgery, and statistically examine the association of these pathways to the 3D shape of the spine at two-year follow-ups. An underlying assumption of this approach is that the biomechanical changes induced during the surgery can be described using a combination of the 3D shape of the spine at early post-operative and the location of the vertebral levels that are immobilized via a metal rod and are fused within two-year post-operative thus changing the mechanical properties of the spine in the instrumented section. The approach conducts a physical low-dimensional modeling of the scoliotic spine using the geometrical characteristics of the 3D curve e.g., the X, Y, Z centroids of 17 vertebrae e.g., 51 parameters. Then a statistical model for reducing the dimension from 51 parameters to a limited number of the cluster indices for each patient is employed.

To identify the pathways and predict the outcome, the combination of the 3D curvature of the spine before surgery (the pre-op clusters) and the biomechanical impact of the surgery on the spinal alignment (the early post-op clusters), plus the fusion levels, significantly determine the 3D shape of the spine at two-year follow-ups after surgery (two-year clusters) in the AIS population.

Generation of Spinal Curve

The first step in the system/methods described herein is the generation of a curve of the spine. A 3D curve may be generated from a 3D reconstruction of the spine or 2D curves may be generated directly from 2D medical images of the spine.

Figure 1C:
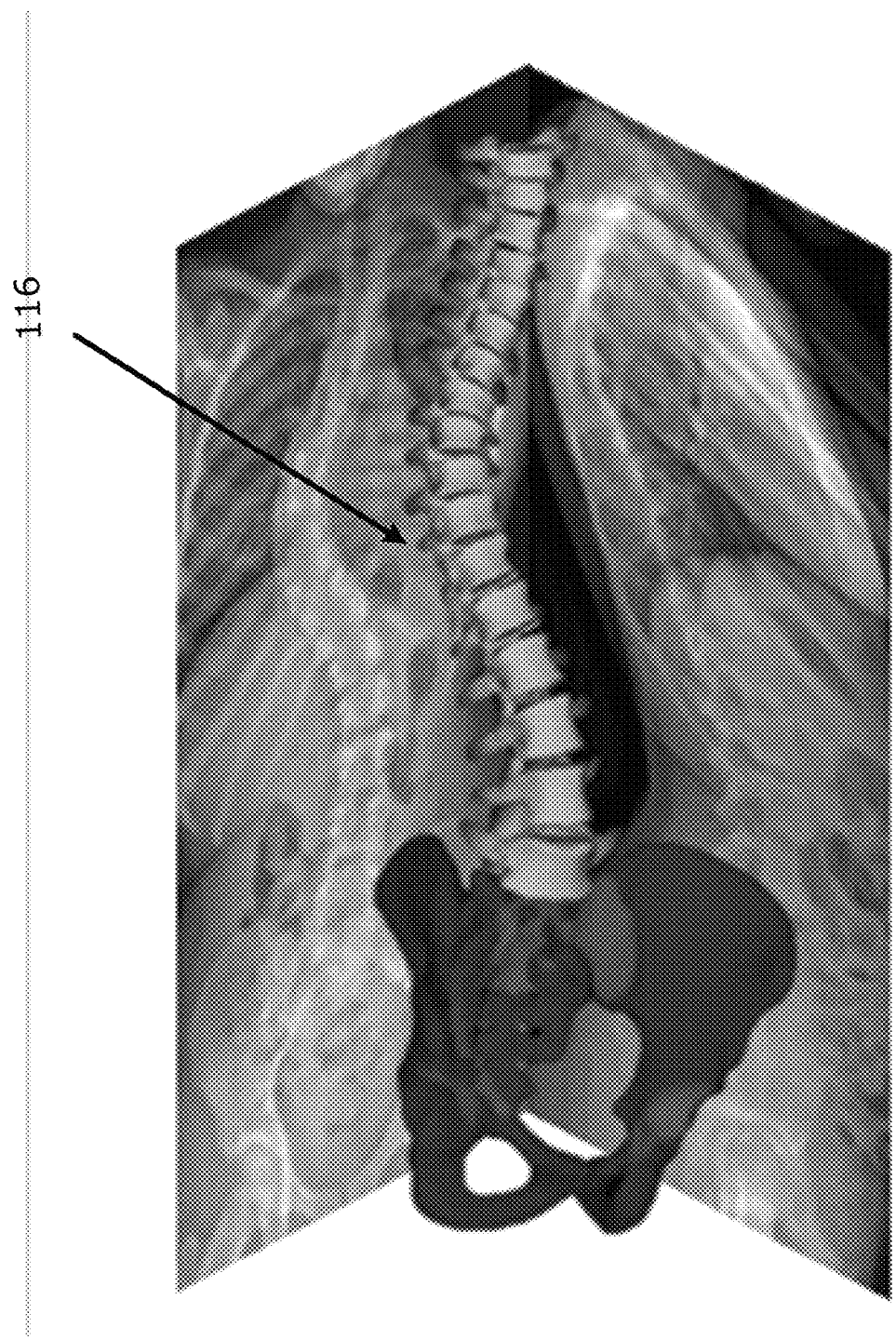
FIG. 1C is a 3D image processing of a spine suffering from scoliosis, according to an aspect of the disclosure.

FIG. 1C shows an example of a 3D reconstruction of a spine 116 suffering from AIS. This 3D reconstruction may be performed by capturing multiple 2D radiology/sonography images (e.g., X-ray images, magnetic resonance images (MRI), ultrasound images, etc.) of the spine from various angles around the front, back, and sides of the patient, and then using an algorithm to conduct image processing (e.g., 3D reconstruction) of the spine based on the 2D images of the spine.

In one example, the 2D images may be captured by a standard X-ray machine that is manually positioned by a radiology technician at various locations around the patient's torso while capturing X-ray images. In other example, the 2D images of the spine may be captured automatically by a machine that automatically moves (e.g., rotates) around the patient's torso while capturing X-ray images from various angles. The patient may be able to lay, sit or stand inside such a machine, and then exit when the images are captured.

In one example, the 2D images are processed by an image processing algorithm to generate a 3D image (e.g., reconstruction) of the spine, where 3D features of the spine are then extracted to produce a 3D curve that can be used for the analysis hereafter. In this method, after the clusters of the 3D spinal curves are determined in the training step for a number of patients, for any new patient, that has not been included in the training process, the features of the spine can be extracted from the 3D reconstruction of the new patient's spine to produce a new 3D curve. These features are then matched to an existing 3D cluster to each new patient.

Figure 1D:
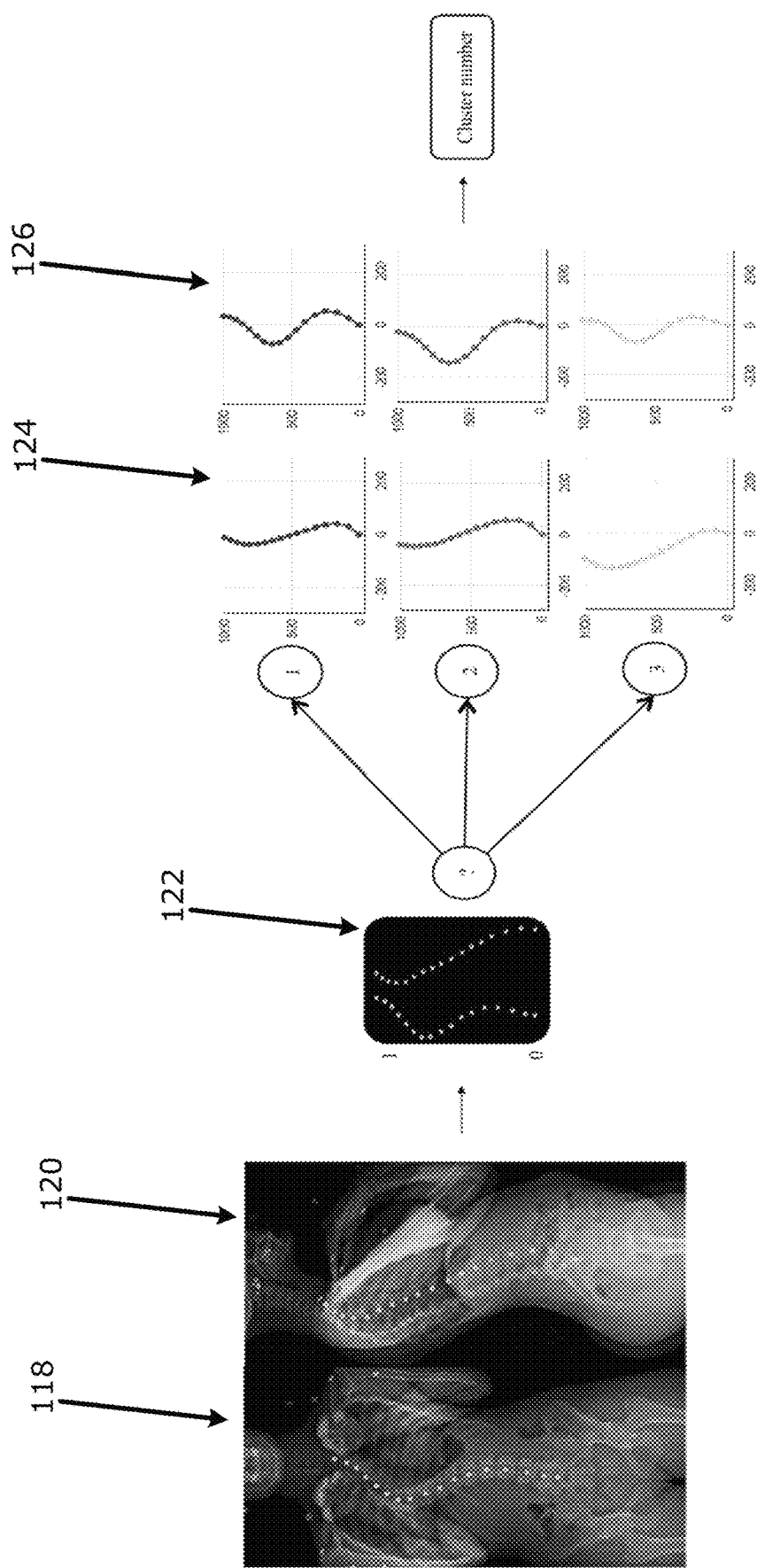
FIG. 1D is a graphical flowchart describing the training and/or outcome prediction process using 2D curves, according to an aspect of the disclosure.

It is noted that 3D reconstruction (e.g., generating a 3D image) is an intermediate step that is not necessary to produce the 3D curve. 2D curves may be generated directly from the 2D medical images. An example of 2D curve generation directly from the medical images and the resultant clustering is shown for a patient X in FIG. 1D. In a first step, medical images are captured for both frontal view 118 and sagittal view 120 of patient X. The image processing algorithm determines a point(s) (i.e. landmark(s)), such as a center point on each select vertebrae to produce frontal and sagittal 2D curves 122 that together, represent the 3D curvature of the spine. These features are then matched to the 2D projections of one or more of the existing clusters in order to assign a 3D cluster to each new patient without the need for 3D image processing. This method is based on the premise that for each unique 3D spinal curve, a unique pair of frontal and sagittal projections exists. Thus by matching pairs of 2D frontal and sagittal spinal curves of a new patient to the existing 2D projection of the 3D clusters, a cluster number can be assigned to the patient.

For example, during the training process, these frontal and sagittal curves 122 of patient X may be compared to frontal and sagittal curves of other patients to produce clusters 1, 2 and 3. Then, during the outcome prediction process, these frontal and sagittal curves 122 of patient X may be compared to frontal 124 and sagittal 126 curves of established clusters e.g., 1, 2 and 3 to determine a best match for patient X (e.g., determine a cluster match for patient X).

In yet another example, the 2D frontal and sagittal curves 122 may be combined to generate a 3D curve. The algorithm may then perform the clustering using the 3D curves rather than the 2D curves.

Hardware

In general, the system/methods described herein have three stages (e.g., training, outcome prediction and surgery). FIG. 2A is a view of a system that can be used in one, two or all three of these stages.

As shown in FIG. 2A, the system includes imaging device 204 (e.g., stereoradiography X-ray machine, MRI machine, etc.), computer 206 (personal computer, cloud computer, etc.), and optional surgical robot 210 for performing surgery on patient 202 on operating table 208. As described above, the system may be used for all three stages (training, outcome prediction, and surgery).

For the training process, patient 202 enters imaging device 204 which captures medical images (e.g., X-rays) of the patient's spine from various angles. These images are captured pre-op and at post-op for patient 202. The images are then processed by computer 206 to train the outcome prediction algorithm. Alternatively, the images can be processed by imaging device 204 which may have image processing capabilities. Computer 206 may be a standalone personal computer, a computer integrated into imaging device 204, or a cloud computer(s). The training process groups the spines of multiple (e.g., tens, hundreds, etc.) patients into pre-op and post-op groups, also referred to as clusters, based on similarities in their physical characteristics, and associates a probability for obtaining a post-op result based on the pre-op images (e.g., if a patient has a certain pre-op shaped spine, the system determines a probability of obtaining a post-op shaped spine if certain surgical methods are used). Further details of the training process are described in reference to FIG. 4A.

For the outcome prediction process, a similar approach is taken. For the outcome prediction process, patient 202 enters imaging device 204 which captures at least two orthogonal images of the patient's spine. These images are captured pre-op for patient 202. The medical images are then processed by computer 206 using the trained prediction algorithm to extract the features for analyzing the spinal curvature. Specifically, the pre-op images for patient 202 are compared to the existing pre-op images in the groups (e.g., clusters) of the trained outcome prediction algorithm to determine a matching group. The outcome prediction algorithm then predicts a number of post-op results that are likely for patient 202 based on the specific surgical methods (e.g., a probability that the patient will achieve a certain post-op result is predicted). Further details of the outcome prediction process are described in reference to FIG. 5.

For the surgery process, the surgical methods associated with the predicted results are used during the surgical procedure on patient 202. In one example, the surgical predicted surgical methods are displayed to the surgeon and followed by the surgeon during the surgical procedure. In another example, the predicted surgical methods may be used by a surgical robot 210. For example, the predicted surgical methods generate instructions for controlling surgical robot 210 during the surgical procedure. Although not shown, the surgical robot includes a controller that receives instructions from the outcome prediction algorithm and controls the robot arm accordingly.

Figure 2B:
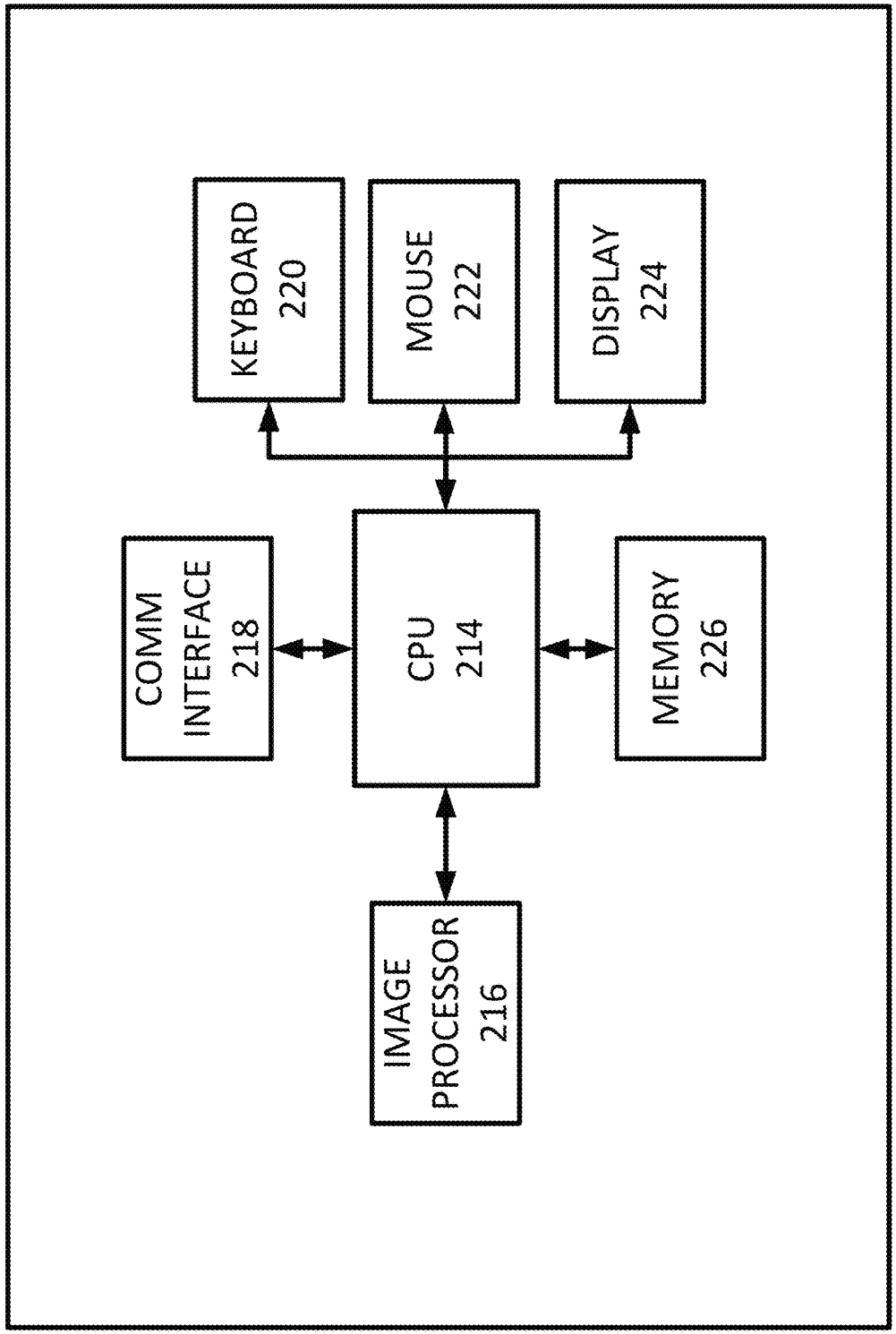
FIG. 2B is a view of a computer for training the outcome prediction algorithm and performing outcome prediction, according to an aspect of the disclosure.

As described above, the computer for performing the training and outcome prediction process may be a standalone PC 206, may be integrated into imaging device 204, or may be a cloud computer(s) or personal portable devices such as a smartphone, tablet and the like. In any such scenario, FIG. 2B is a view of a computer 212 for performing the training and/or the outcome prediction process. Among others, computer 212 may include a central processing unit (CPU) 214 for controlling the overall functioning of the computer, memory 226 for storing software instructions and other data (e.g., patient images, spinal measurements, etc.), keyboard 220, mouse 222 and display 224 for allowing a technician to interact with the computer, communication interface 218 which may be wired (e.g., Ethernet, USB, etc.) and/or wireless (e.g., WiFi, Bluetooth, etc.). Computer 212 may also include a dedicated image processor 216 for processing the patient's spinal images during the training and outcome prediction process.

Measureable Spinal Characteristics

Figure 3A:
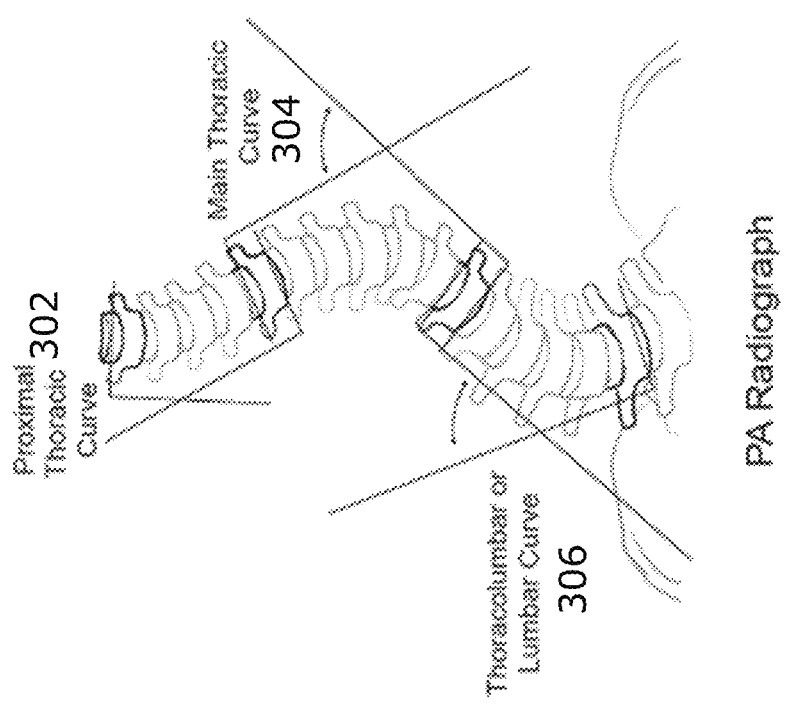
FIG. 3A is a view of measureable spinal characteristics, according to an aspect of the disclosure.
Figure 3B:
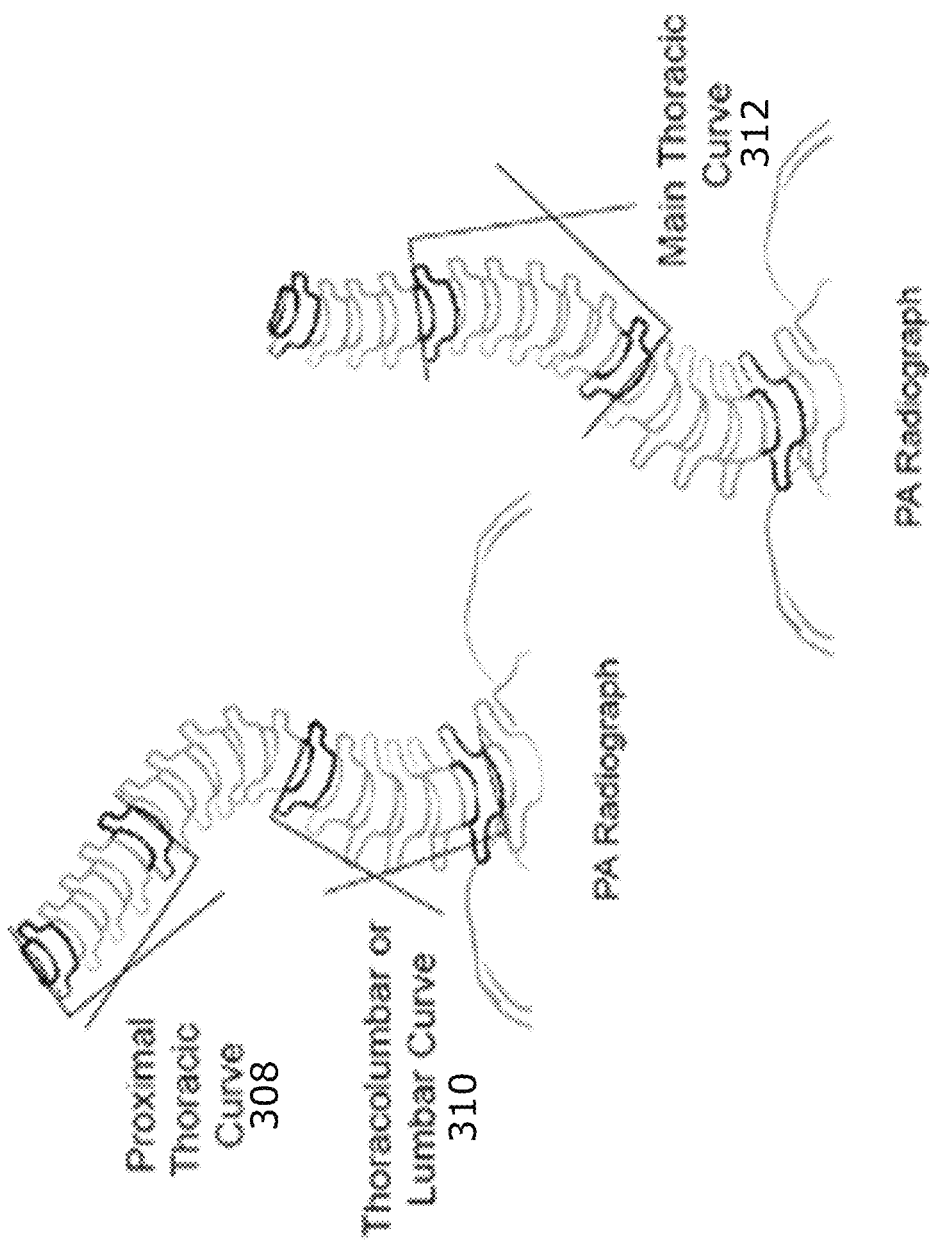
FIG. 3B is another view of measureable spinal characteristics, according to an aspect of the disclosure.
Figure 3C:
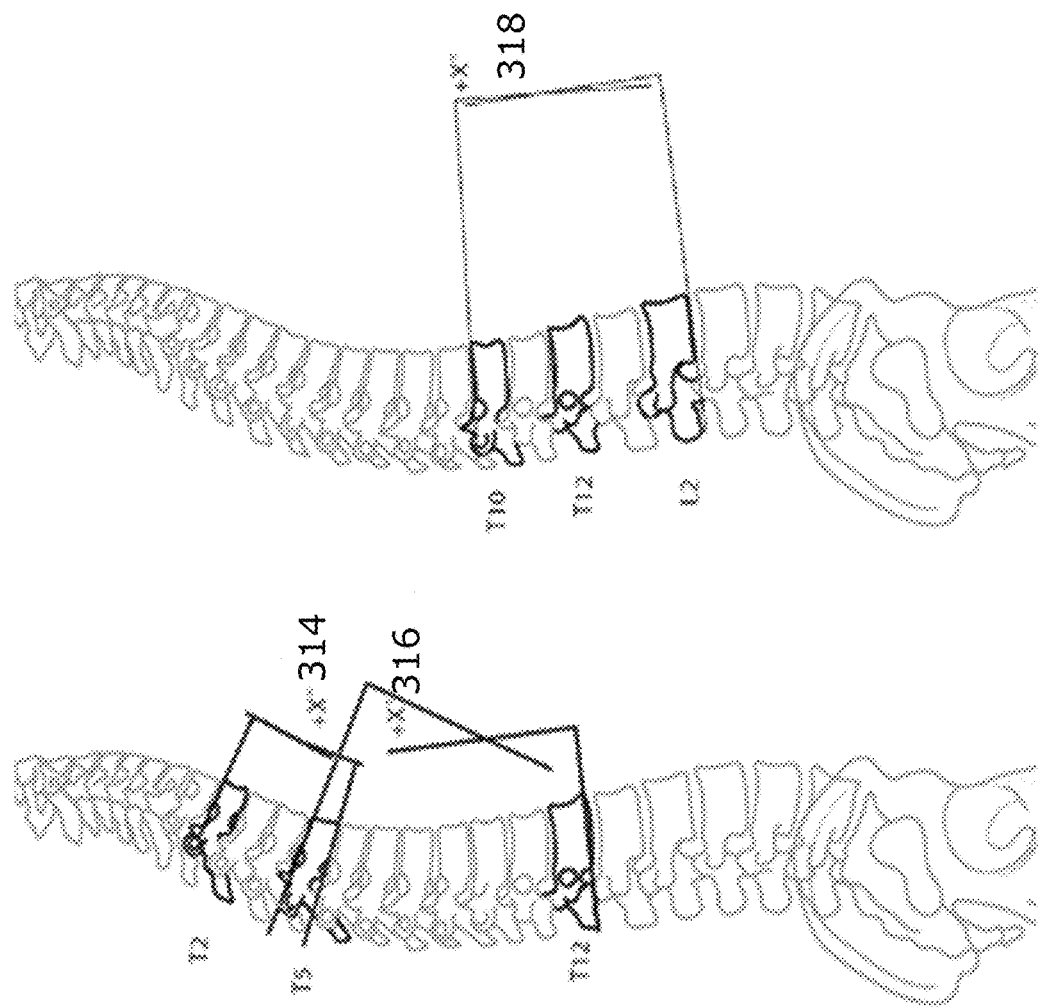
FIG. 3C is yet another view of measureable spinal characteristics, according to an aspect of the disclosure.

Before describing the training process and outcome prediction process in detail, it may be helpful to understand measureable characteristics of the spine. These measureable characteristics include but are not limited to Coronal/Sagittal Cobb angles, Coronal/Sagittal Bends, etc. of the spine. FIG. 3A is a view of measureable Coronal Cobb angles 302, 304 and 306. FIG. 3B is a view of measureable Coronal bends angles 308, 310 and 312. FIG. 3C is a view of measureable Sagittal Cobb angles 314, 316 and 318. Although not described, other spinal measurements are also possible. Rather than measuring all of these various angles and bends, which can be tedious and prone to error, the training and outcome prediction algorithm described herein generates a 3D curve of the spine. This 3D geometrical curve represents the spine and all of its inherent angles/bends, and therefore can be analyzed as a whole. As mentioned above, the 3D curve can be extracted from the 3D reconstruction of the spine or directly from the features of the 2D medical images without generating the 3D reconstruction of the spine in order to assign a cluster number based on the 3D characteristics of the spine to each patient. For example, the 2D curves shown in FIG. 1D could be combined to generate the 3D curve without performing the optional 3D reconstruction. In yet another example, the training and outcome prediction algorithm could utilized multiple 2D curves rather than a 3D curve.

Training Process for Evaluating Surgical Methods

Figure 4A:
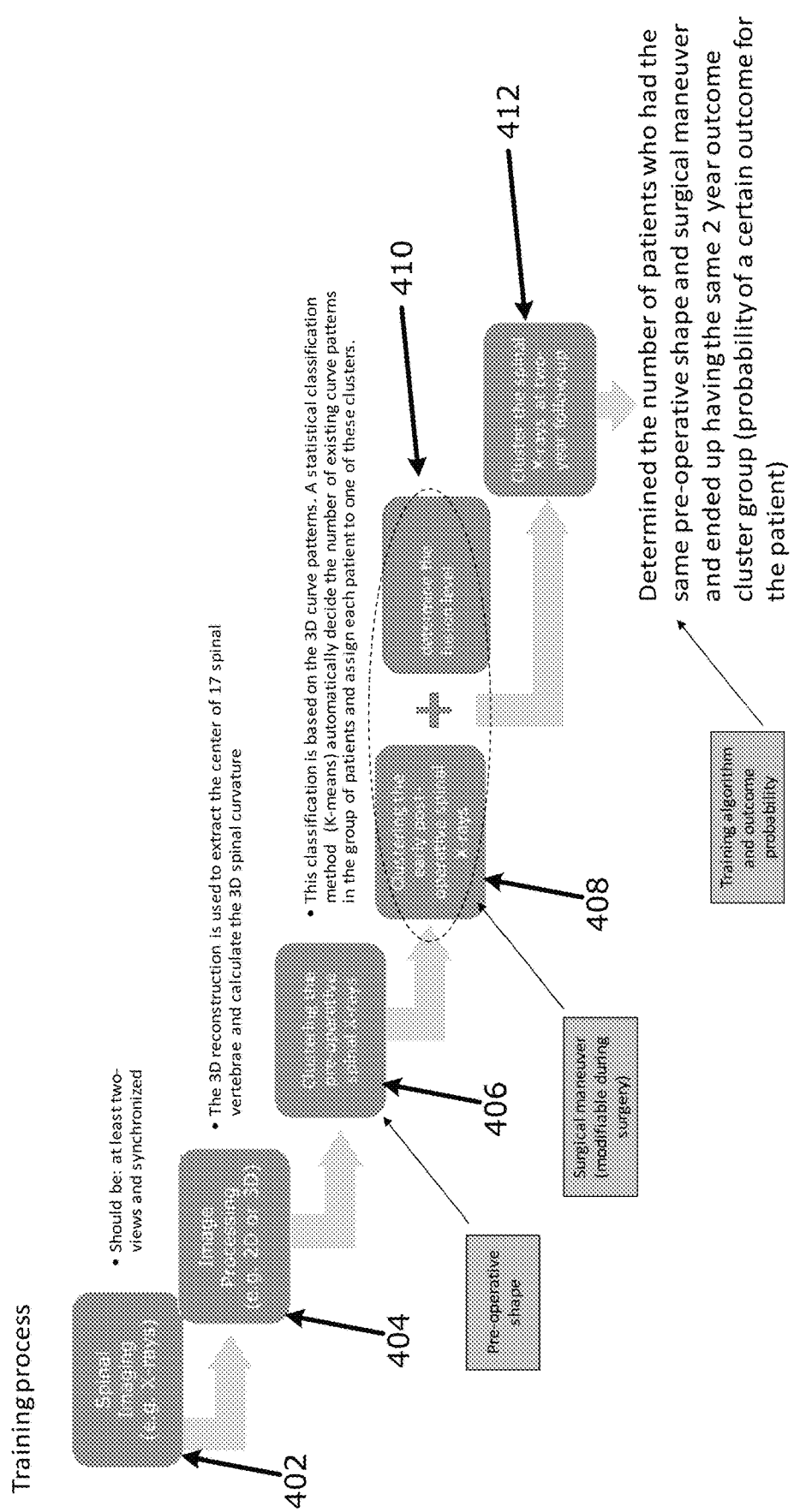
FIG. 4A is a flowchart describing the training process for training and outcome prediction algorithm, according to an aspect of the disclosure.

As described above, the training process trains the outcome prediction algorithm based on a group of patients that have already had spinal surgery and have known results. FIG. 4A is a flowchart describing the training process.

In step 402, pre-op and post-op spinal medical images (e.g., X-rays from different angles) for a number of patients are captured and then analyzed (e.g., image processed) by computer 212 in step 404. The image processing, in this example, extracts geometrical features (e.g., 2D or 3D) of the spinal curve in the patient. The spinal curve (e.g., 2D curve or 3D curve) is then analyzed by computer 212 in step 406 to cluster (e.g., group) the pre-op images into a number of clusters having similar characteristics (e.g., 3D curve with similar geometrical characteristics are grouped together). A similar clustering process is performed by computer 212 in step 408 on the early post-op images (e.g., images taken shortly after surgery) for the patients. In addition, this clustering step may take into account a vertebral fusion level 410 of the spine that was performed during the surgery (e.g., which vertebrae where included in the surgery). This fusion information may be helpful, because fusion affects the overall alignment and flexibility of the spine. In step 412, computer 212 clusters post-op images taken a significant time after surgery (e.g., 2 years after surgery). The training algorithm develops "treatment paths" from pre-op clusters to post-op clusters and assigns a probability to each treatment path. This allows the algorithm to predict a 2 year outcome for a pre-op spine of a new patient to a certain degree of accuracy, assuming similar surgical techniques are utilized (e.g., if a new patient has a similar shape to the spines in one of the pre-op clusters, and the same surgical techniques are used, the post-op results are expected be similar for the new patient).

Figure 4B:
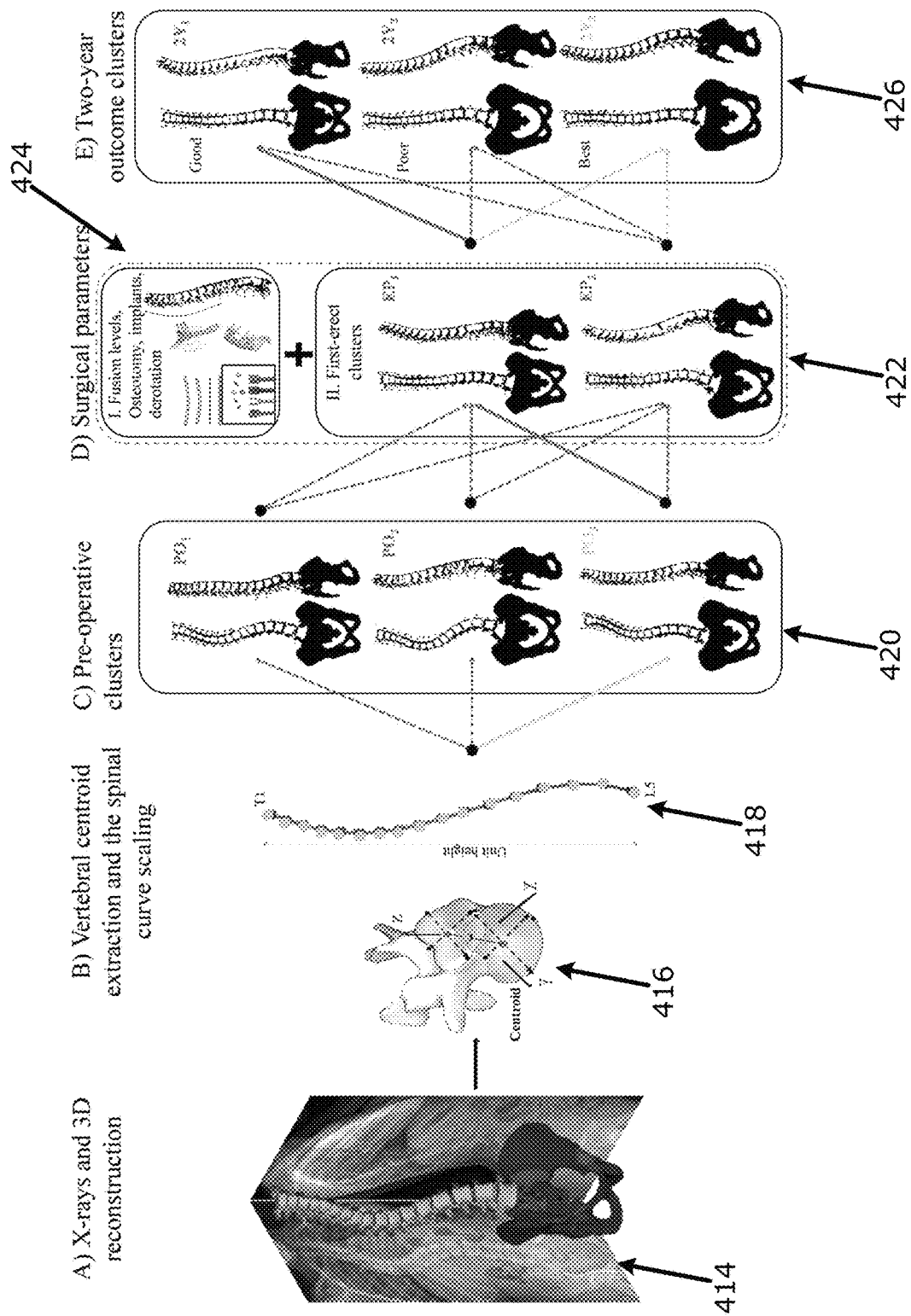
FIG. 4B is a graphical flowchart describing the training process in FIG. 4A, according to an aspect of the disclosure.

FIG. 4B is a graphical flowchart describing the training process in FIG. 4A. In step 414 computer 212 performs image processing (e.g., 3D analysis) of the spine in the captured medical images. In step 416, computer 212 determines a point(s) (i.e. landmark(s)) on select vertebrae (e.g., a centroid of the vertebrae). In step 418, computer 212 determines a 3D features of the spine (e.g., locations, orientation and alignment of the vertebrae), characterizing its 3D geometrical curve. For example, a 3D spline curves may be generated by interpolating the vertebrae centroids. A pre-op, early post-op and two-year 2Y post-op spline curve are generated by computer 212 for each patient analyzed in the training process. At step 420, computer 212 clusters the pre-op 3D curves, developed from the medical images of the spine into multiple clusters (e.g., 3 clusters as shown) based on physical similarities between the 3D curves. At step 422, computer 212 clusters the early post-op spline curves into multiple clusters (e.g., 2 clusters as shown) based on physical similarities between the 3D curves and based on one of more of parameters 424 that include, but are not limited to, fusion levels, Osteotomy, implants and derotation used during the surgery. At step 426, computer 212 clusters the 2Y post-op 3D curves into multiple clusters (e.g., 3 clusters as shown) based on physical similarities between the curves. Treatment paths having associated probabilities are generated between the clusters in steps 420, 422 and 426. These treatment path probabilities can be used during the outcome prediction process which is described later.

Figure 4C:
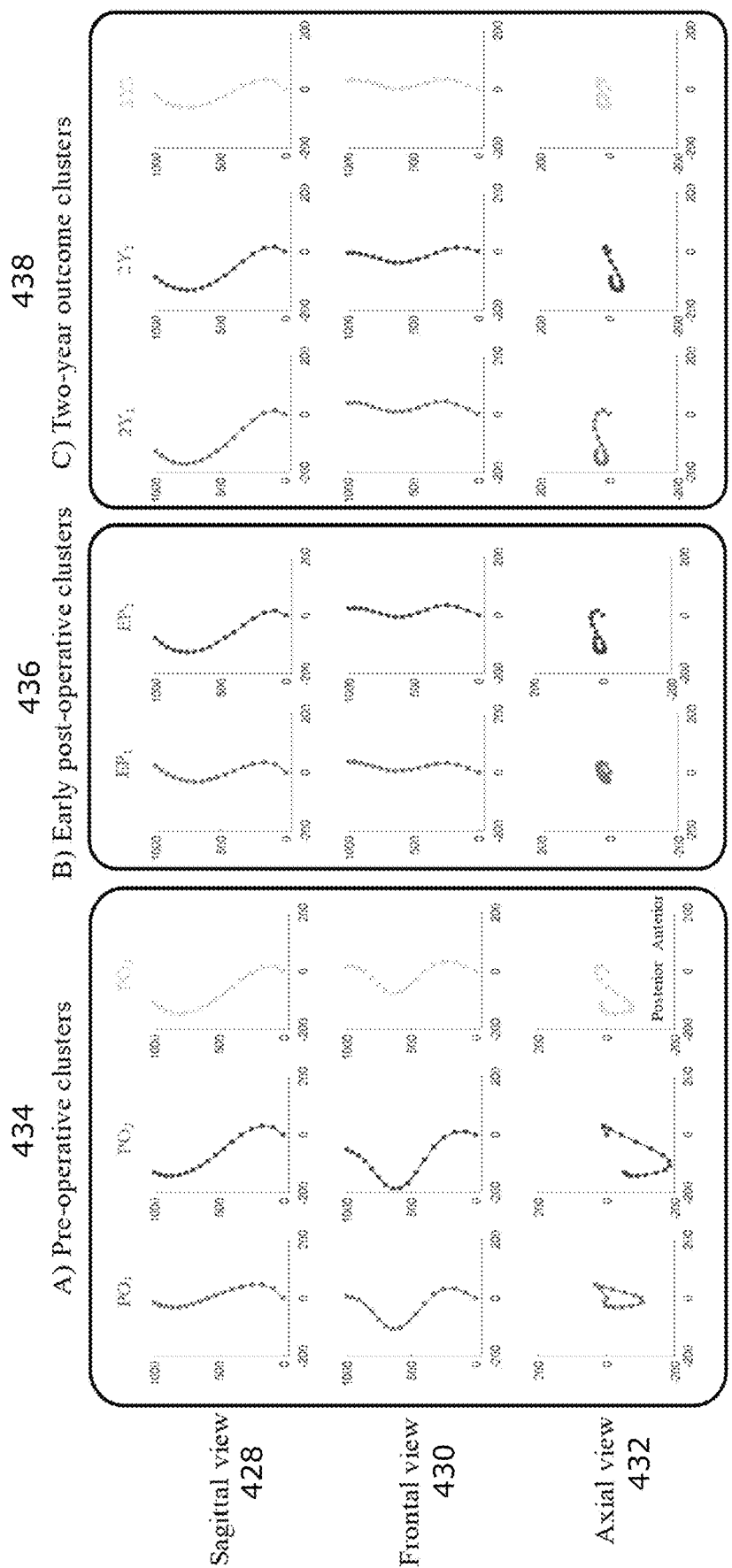
FIG. 4C is a view of the spine clusters in FIG. 4B, according to an aspect of the disclosure.

FIG. 4C shows various views of the 3D curves for each spine cluster in FIG. 4B. Specifically, window 434 shows Sagittal view 428, Frontal view 430 and Axial view 432 of the 3 pre-op clusters in FIG. 4B. Window 436 shows Sagittal view 428, Frontal view 430 and Axial view 432 of the 2 early post-op clusters in FIG. 4B. Window 438 shows Sagittal view 428, Frontal view 430 and Axial view 432 of the 3 two year post-op clusters in FIG. 4B.

Figure 4D:
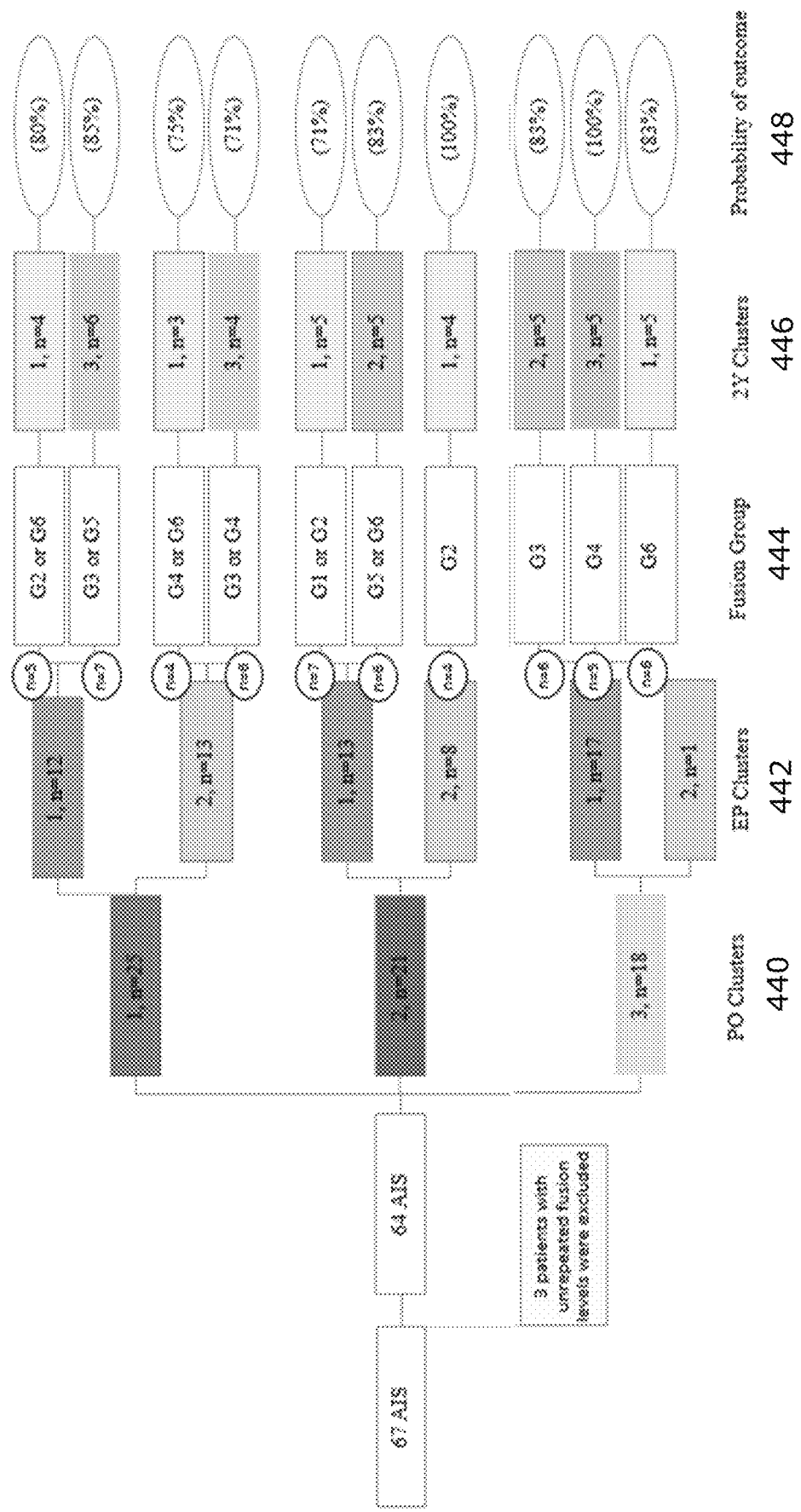
FIG. 4D is a graphical flowchart describing a training process performed on 67 patients, according to an aspect of the disclosure.

In general, during the training process of the algorithm, the 3D spinal curvature and its describing components are normalized across a cohort of AIS patients. Various algorithms may be used to accomplish the analysis and grouping performed during training. For example, FIG. 4D shows a training process for developing the treatment paths from the pre-op clusters to the 2Y post-op clusters. In this example, a total number of 67 AIS patients with a main right thoracic curve (Lenke 1 and 2) age between 10-18 years were selected retrospectively. All patients had biplanar spinal stereoradiography at three visits: the medical images were registered within one-week pre-op (PO), early (within a month) post-op (EP), and at two-year after surgery (2Y). The exclusion criteria were previous spinal surgery, vertebral supernumerary, neuromuscular conditions, and musculoskeletal conditions other than scoliosis. Twenty non-scoliotic adolescent verified by bi-planar spinal medical images and clinical examinations were included as the control group.

The 3D image analysis for example, using a commercially available software, SterEOS 2D/3D (EOS imaging, Paris, France) extracted the 3D features of the spine. In this example, 3D reconstruction of the vertebral bodies was used to calculate the 3D coordinates of the vertebral centroids (X, Y, Z) in the global coordinate system of the spine. An isotropic scale factor, in three dimensions, was used to normalize the spinal height [0-1] of each patient in the AIS cohort. The same process, e.g., 3D analysis of the medical images, center extraction, and scaling was performed for the control cohort. The Z levels of the average scaled spines in controls was used to interpolate the (X, Y) coordinate of the consecutive vertebral centroids in the AIS cohort, resulting in obtaining (X, Y) coordinates at equal Z levels for all the patients.

A statistical clustering method (e.g., K-means clustering) was used to cluster the 3D coordinates of the vertebral centroids of the scaled scoliotic spines. Given that the Z coordinates of the T1-L5 spinal vertebrae for all patients are the same (as described above) the clustering is performed only on (X, Y) coordinates of the vertebrae of all patients. The number of clusters was determined by calculating the silhouette values using the Euclidian distances. The K-means cluster analysis was performed on the scaled PO to generate 3 PO clusters 440 (25 spines in cluster 1, 21 splines in cluster 2 and 18 spines in cluster 3), 2 EP clusters 442 (the spines from PO clusters 1, 2 and 3 are split into two EP clusters), and 3 2Y clusters 446 (the spines from EP clusters 1 and 2 are split into three 2Y clusters). In this example, the algorithm determines clusters of patients at the three time-points.

The fusion levels based on the upper and lower instrumented vertebrae (UIV and LIV) were recorded using the patient's surgical notes. All available fusion levels were determined and group numbers (e.g., G1-G6) were assigned to each distinct fusion level 444, e.g., same UIV and LIV. The treatment paths were then determined using the PO cluster number ($PO_i$), EP cluster number ($EP_j$), and fusion level group ($F_m$) 444, constructing a three-level path presented as $PO_i$-$EP_j$-$F_m$.

A regression (e.g., multinomial regression) model was used to predict the outcome 448 cluster at two-year ($2Y_k$) from the treatment paths for the cohort as follows:

$f(PO_i, EP_j, F_m) \rightarrow 2Y_k$ where i,j,k are the cluster number at each given time point and m is the fusion group. The number of patients in each treatment path that had the same $2Y_k$ was calculated to determine the occurrence of certain outcome 448 for each of the identified treatment paths.

To determine the differences between the clusters in terms of clinically measurable variables, the clinical measurements of the patients at PO, EP, and 2Y were measured and compared between clusters at each time-point, using the appropriate statistical method. These variables are the parameters that either can be directly extracted from the medical images of the spine or via a commercial software (SterEOS 2D/3D, EOS imaging, Paris, France). These clinical parameters are proximal thoracic Cobb (PTC), proximal thoracic rotation (apical) (PTR), main thoracic Cobb (MTC), main thoracic rotation (apical) (MTR), lumbar Cobb (LC), lumbar rotation (apical) (LR), thoracic kyphosis (TK both between T1-T12 and T4-T12), lumbar lordosis (LL), pelvic incidence (PI), sacral slope (SS), pelvic tilt (PT), frontal balance (FB), and sagittal balance (SB).

The training process shown in FIG. 4D generates various treatment paths from the PO clusters to the EP clusters and then to the 2Y clusters. Each of these paths has an associated probability of achieving the 2Y results when following similar surgical techniques.

Outcome Prediction Process for Choosing Surgical Methods

FIG. 5 is a flowchart describing the outcome prediction process that may be implemented once the training process is complete. In step 502, a new patient is imaged (e.g., X-rayed) and computer 212 performs image processing (e.g., 3D reconstruction) of their spine in a manner similar to that described above in the training process. In step 504, computer 212 determines the shape of the spine by generating a curve (e.g., 2D curve or 3D curve) based on the image processing of the medical images in a manner similar to that described above in the training process. It is noted that the image processing may include generating a 3D curve from a 3D reconstruction of the spine. However, 3D reconstruction is optional, and therefore the image processing can generate the 3D curve directly from the 2D medical images. In yet another example, the image processing may generate and utilize multiple 2D curves in place of the 3D curve.

In either case, in step 506, computer 212 matches the spine curve (e.g., 2D or 3D) to one of the pre-op clusters determined during the training process. In one example, the cluster having a curve most similar to the patient's spinal curve is chosen from the possible clusters. This may be performed by machine learning and artificial intelligences method where the spinal curve features are compared to each existing cluster and a cluster number can be assigned automatically by choosing the best match. In step 508, computer 212 then follows the various treatment paths for the matching pre-op cluster (e.g., the possible paths through the EP clusters and to the 2Y clusters) and lists the possible 2Y outcomes and their associated probabilities.

For example, if a patient's spinal curve matches PO cluster 1 (see FIG. 4D), there are four possible treatment paths to reach one of two different 2Y clusters (e.g., 2Y cluster 1 and 2Y cluster 3). If the surgeon determines that 2Y cluster 3 would be more beneficial to the patient, then the outcome prediction algorithm is restricted to two paths that have fusion groups resulting in 2Y cluster 3. The first treatment path has an 85% chance probability to lead to a 2Y outcome of cluster 3 when fusion groups G3 or G5 are selected. The second treatment path has a 71% chance probability to lead to a 2Y outcome of cluster 3 when fusion groups G3 or G4 are selected. Either treatment path may be chosen for surgery. Both the first and second treatment paths have associated surgical methods that were performed to lead to the respective 2Y results. Among others, the surgical methods include fusion group, vertebrae selection, rod placement, screw placement, etc. This information may then be used to instruct either the surgeon or a surgical robot in performing surgery on the patient such that similar results can be achieved.

Probabilistic Model for Outcome Prediction

The above-described K-means clustering method is a hard classification method to assign each individual's spine to a cluster. However, borderline patients may not fit neatly into a single classification, which could impact the outcome prediction accuracy of the model. Application of a method for developing a soft probabilistic classification may therefore be beneficial. This probabilistic classification promotes an improved knowledge-based outcome prediction by assigning belonging weights to each data point. This allows determination of surgical solution for borderline patients. For example, rather than classifying a patient into a single class (e.g. class A), the system could indicate probabilities that a patient falls into more than one classification (e.g. 70% class A and 30% class B).

Figure 6:
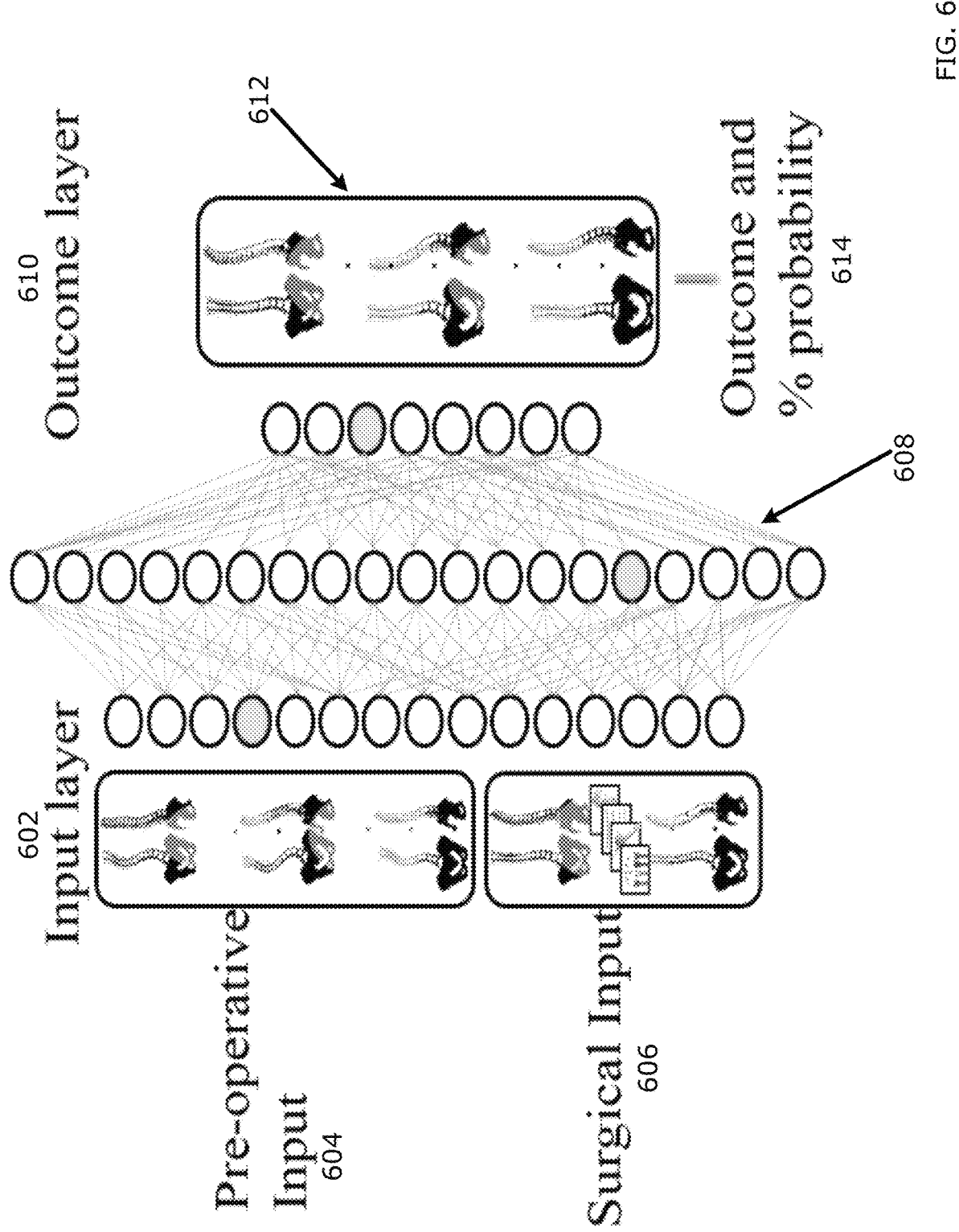
FIG. 6 is a graphical flowchart describing a probabilistic model for outcome prediction, according to an aspect of the disclosure.

Using a soft clustering method (e.g. expectation-maximization (EM)) by incorporating an initial classification, the 3D spines at different time-points could be classified. This method allows the patients to be assigned to a varying number of clusters based on a probabilistic "belonging score" or "different degree of belief." A probabilistic fuzzy regression, for example, may then be used to predict the outcomes based on the input variables. The predictive variables, pre-operative shape classification and surgical factors (which may include the fusion levels), predict the two-year outcomes. In addition to the radiographic variables and surgeon modifiable factors, patient demographics, other patient related variables such as weight, height, body mass index (BMI), and comorbidities may be included as the predictors of the outcomes. An example of a probabilistic model for outcome prediction is shown in FIG. 6, where pre-operative input 604 and surgical input 606 are input at the input layer 602. A fuzzy neural network (NN) 608 explores the association between the variables and predicts the outcome 612. The shaded dots in NN 608 show an example for a patient's probabilistic outcome which is output as an outcome 612 and percent probability 614 in outcome layer 610.

Figure 7:
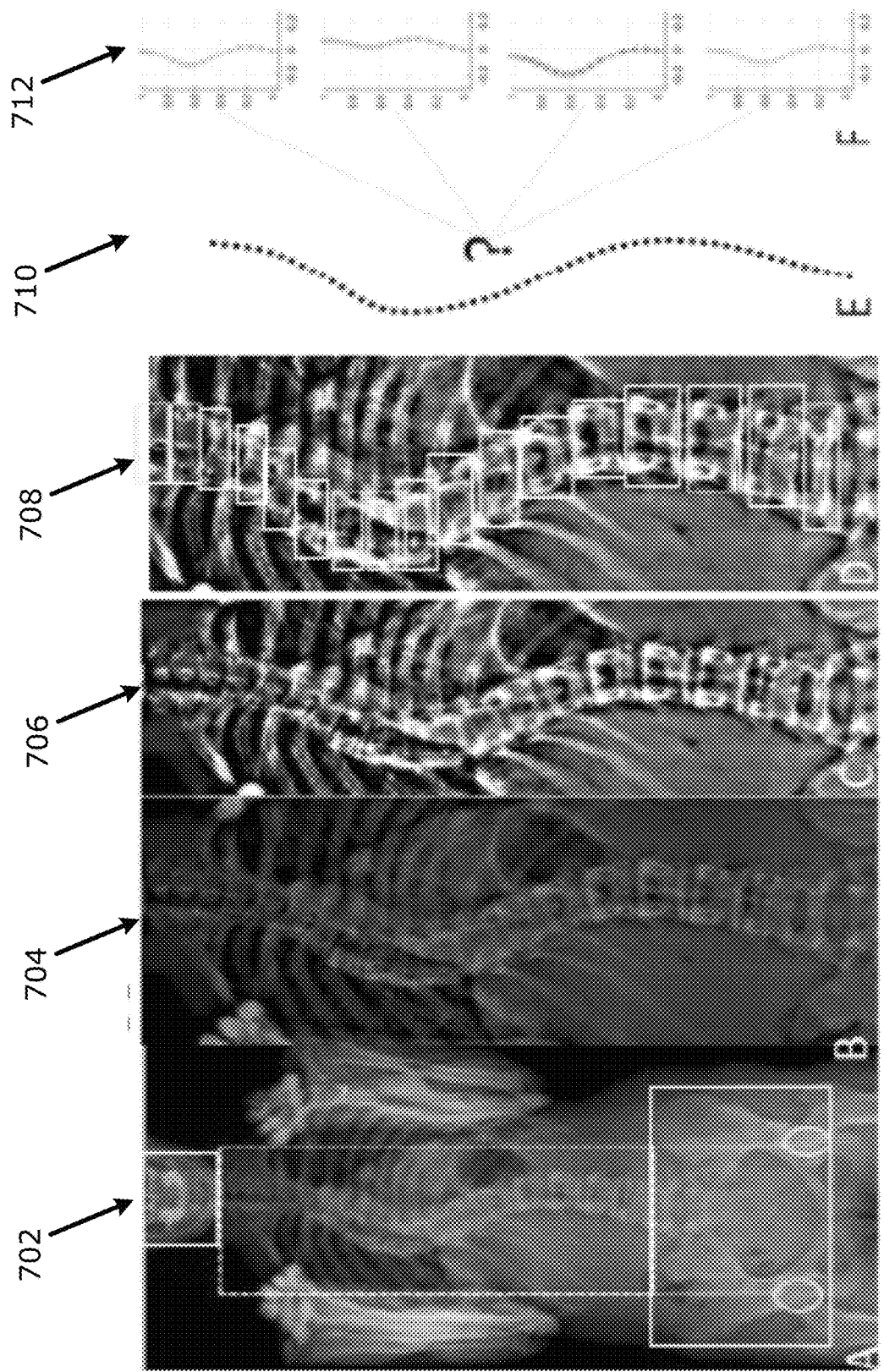
FIG. 7 is a graphical flowchart describing automated image processing for class assignment, according to an aspect of the disclosure.

In implementing both hard clustering and soft probabilistic classification, image processing and object detection of spinal X-rays, based on exploiting the appearance and shape features of the vertebral bodies and prior knowledge on the position of the spine (vertebral bodies) with respect to more identifiable anatomical landmarks (e.g. pelvis, femoral head, cervical spine, and the skull) (702 in FIG. 7), can be used to determine the 3D spinal curvature. This allows a fast identification of the vertebral bodies (704 in FIG. 7), which after applying filters (706 in FIG. 7), a linear neural network layer in the training series and a patch by patch analysis (708 in FIG. 7), the spinal curve is determined (710 in FIG. 7). A cluster number then can be assigned to the detected curve through pattern recognition by comparing the new curve to the existing cluster patterns (712 in FIG. 7). This approach allows a low computational cost process that can communicate with a hand-held device, appropriate for clinical application.

Figure 8:
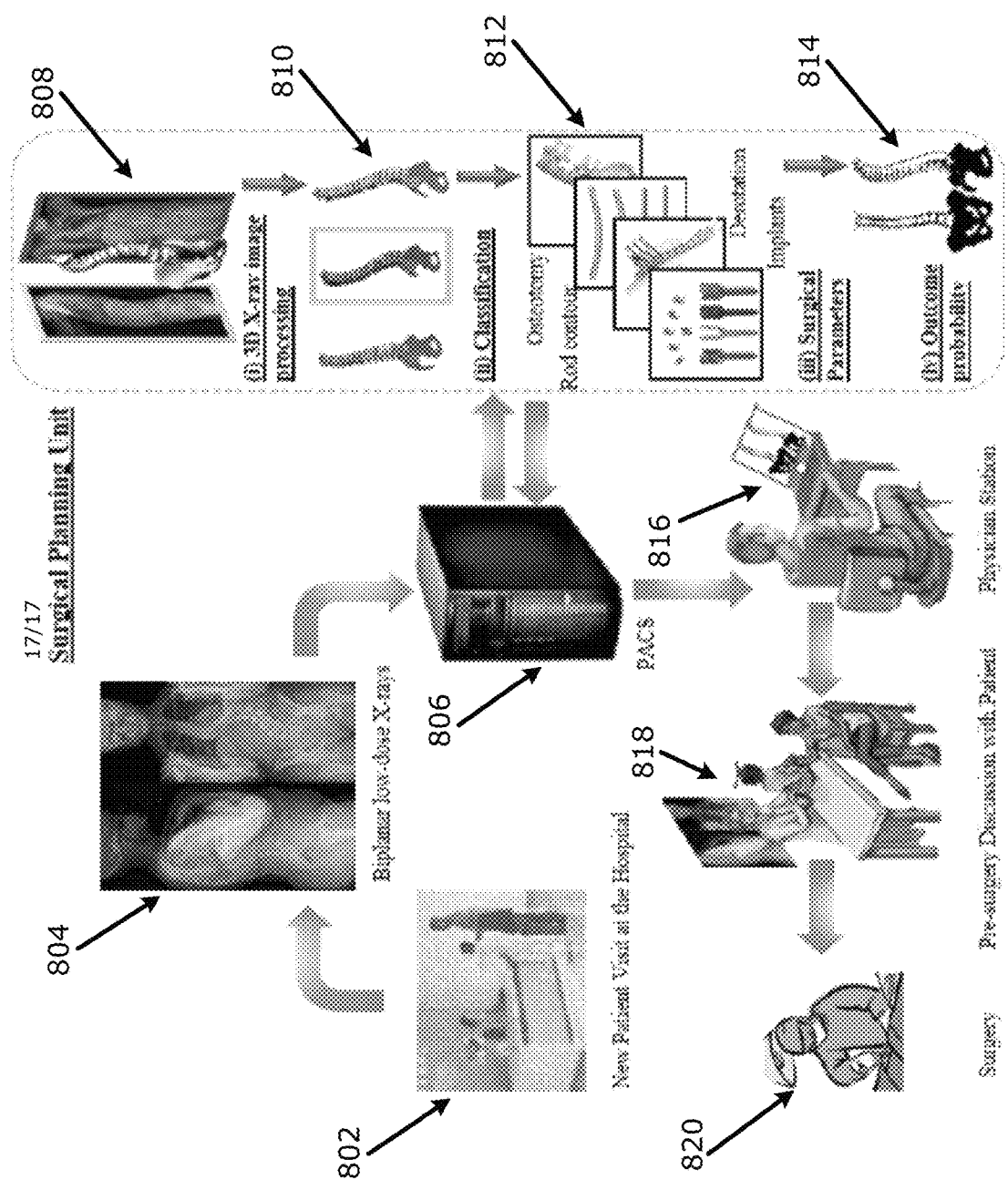
FIG. 8 is a view of a schematic of the system in a clinical setup, according to an aspect of the disclosure.

As shown in FIG. 8, the image processing suite develops an automated platform known as the surgical planning unit (SPU) for patient processing based on the parameters to develop the probabilistic model. For example, when a new patient visits the hospital (802 in FIG. 8), images of the patient's spine are captured (804 in FIG. 8) and then the images are stored in the picture archiving and communication system (PACS) (806 in FIG. 8). The SPU then performs automated image processing of the spinal images (808 in FIG. 8), patient classification (810 in FIG. 8), identification of the surgical parameters (812 in FIG. 8), and probabilistic outcome computation (814 in FIG. 8). The SPU can also communicate directly with the PACS to make the results available to the physicians (816 in FIG. 8) and act as an assistive tool for pre-surgical communication with the patient and final surgical planning by the surgical team (818/820 in FIG. 8).

As the proposed classification for surgical outcome prediction is based on the overall shape of the spinal curve, application of deep learning and neural networks (e.g. Convolutional neural network (CNN)) can be performed to generate segmentation and detect the candidate regions of the spine automatically. Identifying the spine on the radiographs, the classifier algorithm then assigns a class number based on a criterion of greater similarity. The nearest prototype classifier (NPC) is then used to assign new data points (e.g. patients) to the prototypes. A criterion based on the similarity of the new data and existing clusters allows the generation of new classes when a classification instance in the preceding iteration results in an increase in the inter-class error preset by the algorithm threshold. This iterative learning algorithm can be updated for new patients and allows a dynamic classification based on the new data-points.

The steps in FIGS. 4A, 4D and 5-8 may be performed by the computer 212 in FIG. 2B upon loading and executing software code or instructions which are tangibly stored on a tangible computer readable medium 226, such as on a magnetic medium, e.g., a computer hard drive, an optical medium, e.g., an optical disc, solid-state memory, e.g., flash memory, or other storage media known in the art. In one example, data are encrypted when written to memory, which is beneficial for use in any setting where privacy concerns such as protected health information is concerned. Any of the functionality performed by the computer described herein, such as the steps in FIGS. 4A, 4D and 5-8 may be implemented in software code or instructions which are tangibly stored on a tangible computer readable medium. Upon loading and executing such software code or instructions by the computer, the controller may perform any of the functionality of the computer described herein, including the steps in FIGS. 4A, 4D and 5-8 described herein.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

The invention claimed is:

1. A spinal surgery training system comprising:
   an imaging device configured to:
      capture a plurality of images for each of a plurality of spines;
   a processor configured to:

generate a curve of each spine of the plurality of spines from the respective images based on locations of select vertebrae in each spine;

apply a statistical clustering method to group each of the plurality of spines into one of a number of clusters based on similarity of the generated curves to produce clusters of spines having similarities;

wherein the imaging device and the processor are further configured to perform the capturing, generating, and grouping steps at least once prior to surgery and at least once after surgery to produce pre-operative clusters and their resultant post-operative clusters; and wherein the processor is further configured to assign surgical methods and a probability to each of the post-operative clusters indicating the probability that a spinal shape of the post-operative cluster can be achieved using the surgical methods.

2. The spinal surgery training system of claim 1, wherein the imaging device captures a plurality of medical images of each spine from a plurality of different perspectives, and is at least one of an X-ray machine, or a magnetic resonance imaging machine, or an ultrasound machine.

3. The spinal surgery training system of claim 1, wherein the processor is further configured to:
compute the curve as a three-dimensional (3D) curve;
compute one or more landmarks on select vertebrae;
determine the location of each select vertebrae based on the landmarks; and
determine the alignment and orientation of each select vertebrae based on the locations.

4. The spinal surgery training system of claim 1, wherein the processor is further configured to:
perform cluster analysis on the select vertebrae of each spine to produce the pre-operative clusters and their resultant post-operative clusters.

5. The spinal surgery training system of claim 4, wherein the cluster analysis includes fusion levels of each spine.

6. The spinal surgery training system of claim 4, wherein the cluster analysis is based on flexibility of each spine and geometry of the curve.

7. The spinal surgery training system of claim 1, wherein post-operative clusters are determined at a first time and a second time after surgery.

8. The spinal surgery training system of claim 7, wherein the first time is early post-op, and the second time is two years post-op.

9. The spinal surgery training system of claim 1, wherein each pre-operative cluster results in a plurality of the post-operative clusters.

10. The spinal surgery training system of claim 1, wherein the processor is further configured to:
update the post-operative clusters by performing the statistical clustering method with additional spines.

11. The spinal surgery training system of claim 1, wherein the processor is integrated into the imaging device.

12. The spinal surgery training system of claim 1, wherein the processor is integrated into a surgical robot.

13. The spinal surgery training system of claim 1, wherein the processor is a standalone computer.

14. A spinal surgery outcome prediction system comprising:
a processor configured to:
generate a curve of the spine from at least two two-dimensional (2D) images of at least two different planes, the curve based on locations of select vertebrae in the spine;
compare features of the generated curve to pre-operative curves of one or more pre-operative clusters of other spines, wherein the pre-operative clusters are associated by a probability with post-operative clusters of the other spines, the probability indicating that a spinal shape of the post-operative cluster can be achieved using select surgical methods on a spine that is similar to the spines in the pre-operative clusters;
match the spine to a subset of the pre-operative clusters based on similarities between the spine and the other spines in the pre-operative cluster; and
choose the select surgical methods associated with one of the matching post-operative clusters selected based on the probability.

15. The spinal surgery outcome prediction system of claim 14, wherein the processor is further configured to:
choose the select surgical methods associated with one of the matching post-operative clusters selected based on the flexibility and pre-operative geometry of the spine.

16. The spinal surgery outcome prediction system of claim 14, wherein the processor is further configured to:
choose the select surgical methods associated with one of the matching post-operative clusters selected based on a preferred one of the post-operative clusters.

17. The spinal surgery outcome prediction system of claim 14, wherein the processor is further configured to:
instruct a surgical robot to perform spinal surgery according to the select surgical methods.

18. The spinal surgery outcome prediction system of claim 14, further comprising:
a display device, for displaying the select surgical methods.

19. The spinal surgery outcome prediction system of claim 14, wherein the processor is integrated into the imaging device.

20. The spinal surgery outcome prediction system of claim 14, wherein the processor is integrated into a surgical robot.

* * * * *